US012458595B2

(12) United States Patent
Smith

(10) Patent No.: US 12,458,595 B2
(45) Date of Patent: Nov. 4, 2025

(54) THERMALLY STABILIZED NANOEMULSION

(71) Applicant: Henry J. Smith, Temecula, CA (US)

(72) Inventor: Henry J. Smith, Temecula, CA (US)

( * ) Notice: Subject to any disclaimer, the term of this patent is extended or adjusted under 35 U.S.C. 154(b) by 686 days.

(21) Appl. No.: 16/350,199

(22) Filed: Oct. 15, 2018

(65) Prior Publication Data

US 2020/0113828 A1 Apr. 16, 2020

(51) Int. Cl.

| | |
|---|---|
| ***A61K 39/395*** | (2006.01) |
| ***A61K 9/107*** | (2006.01) |
| ***A61K 45/06*** | (2006.01) |
| ***A61K 47/68*** | (2017.01) |
| ***A61K 47/69*** | (2017.01) |

(52) U.S. Cl.

CPC ............ *A61K 9/1075* (2013.01); *A61K 45/06* (2013.01); *A61K 47/6849* (2017.08); *A61K 47/6851* (2017.08); *A61K 47/6855* (2017.08); *A61K 47/6907* (2017.08)

(58) Field of Classification Search

None

See application file for complete search history.

(56) References Cited

U.S. PATENT DOCUMENTS 5,662,932 A * 9/1997 Amselem ............. A61K 9/1075 424/450

2010/0112077 A1* 5/2010 Desai ................... A61K 31/337 424/499

OTHER PUBLICATIONS

Rao et al., J. Agric. Food Chem 2010, vol. 58, pp. 7059-7066.*

* cited by examiner

*Primary Examiner* — Yunsoo Kim

(57) ABSTRACT

This invention describes of a means of stabilizing lipophilic drugs for long-term storage by incorporating them into a "thermally stabilized nanoemulsion" that has a phase transition temperature that is at or below the body temperature of 37 C and above a storage temperature of 4-8 C. One or more lipid soluble drugs are incorporated into the nanoemulsion at an elevated temperature above the phase transition temperature of the nanoemulsion and then stabilized for extended storage by lowering the temperature to below its phase transition temperature. This causes the nanoemulsion to transform into solid lipid nanospheres entrapping the drug within the solid lipid matrix. Upon rewarming the lipid nanospheres they will reconvert to an oil-in-water nanoemulsion suitable for administration to the patient in need. This invention further discloses disease targeting thermally stabilized nanoemulsions utilizing targeting agents such as antibodies, aptamers, binding peptides, hormones, cytokines and the like, attached to the exterior of the nanodroplets comprising the nanoemulsion.

6 Claims, No Drawings

THERMALLY STABILIZED NANOEMULSION

CROSS-REFERENCE TO RELATED APPLICATIONS

This patent application claims priority to provisional patent application No. 62/606,970 titled "Thermally Stabilized Nanoemulsion" and filed Oct. 16, 2017.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISK APPENDIX

Not Applicable

BACKGROUND OF THE INVENTION

When pharmaceutical drugs are administered to the patient in need several events can occur. Often a significant fraction of the drug is detoxified by the liver or filtered out by the kidneys; and the remaining drug also rapidly penetrates into all the body tissues. Some of the drug reaches its intended target such as for example a tumor and has a therapeutic effect, but most of the drug also reaches and affects normal tissues resulting in adverse side-effects. This means that every small molecule chemical drug has its own characteristic efficacy and safety profile. Pharmaceutical companies expend a tremendous amount of time, money and scientific resources into developing new small molecule drugs that may exhibit better efficacy and safety than current drugs.

There is however, an alternative approach for developing improved drugs. Instead of the traditional method of searching for new chemical drugs this alternative approach teaches using well-established known drugs and incorporating them into nanosized drug delivery vehicles such as liposomes, micelles, nanoparticles, nanocapsules, nanoemulsions, emulsomes and the like. By incorporating the known drug into these nanosized delivery systems it is possible to essentially develop a "new" pharmaceutical that behaves very differently from the predicate drug. For example, when a drug is enclosed within a drug delivery vehicle such as a liposome or a nanoemulsion the drug is no longer quickly filtered out by the kidneys, or detoxified by the liver, or removed by the immune system. This results in more drug being bioavailable for a longer period of time.

The biodistribution of the drug is also markedly affected when it is enclosed within a drug delivery vehicle. For example, when the predicate free drug is injected intravenously into the patient it quickly exits the blood stream and penetrates into all the body tissues; whereas drugs enclosed within a delivery vehicle are potentially capable of remaining within the blood stream for a longer period of time depending upon the size and chemical composition of the delivery vehicle. In general, those delivery vehicles that are smaller than about 200 nm will circulate in the blood much longer than the free drug particularly if the delivery vehicle is coated with chemicals that shield it from being recognized and removed by the immune system of the host.

There are a wide variety of drug delivery vehicles that have been developed and many have shown significant advantages with regard to safety and efficacy of the incorporated drug when compared to the predicate free drug. It is somewhat surprising therefore to note that to date the number of drugs that have been commercialized using this approach is extremely limited. The reason for this is that it has proven to be very difficult to stabilize the majority of drugs for long-term storage without the drug delivery vehicles developing significant leaks. This has made them cost-prohibitive to manufacture and market. There is a thus great need to develop a drug delivery system that can store drugs for a prolonged period of time and still allow for the controlled release of the drug when administered to the patient in need.

This invention discloses a novel drug delivery system that is effective in storing drugs for a prolonged period of time and still allows for the controlled release of the drug in vivo. It teaches the development of a thermally stabilized nanoemulsion that is in the form of an oil-in-water (o/w) nanoemulsion at, or close to, body temperature but which transforms into a finely dispersed suspension of lipid nanospheres when the temperature is lowered to below its phase transition temperature. This traps the incorporated drug within a solid lipid matrix and prevents leakage during long-term storage. Upon rewarming the lipid nanospheres they will reconvert back into a nanoemulsion suitable for administration to a patient in need.

The utility of nanoemulsions and solid lipid nanoparticles as drug delivery vehicles are well-known to those of skill in the art, and there are numerous studies describing the advantages of each delivery system. The novelty of this invention is that it teaches a means of utilizing the phase transition temperature of the nanoemulsion as a means of combining the desirable features of nanoemulsions and solid lipid nanoparticles into a single delivery system. The art is silent on the development and utility of thermally stabilized nanoemulsions as a means of stabilizing drugs for long-term storage, and allowing for the controlled release of the drug when administered to the patient in need.

In one embodiment of this invention the development of a disease targeting thermally stabilized nanoemulsion is disclosed. A disease targeting agent such as an antibody, or aptamer or binding peptide, is attached to the exterior of the nanodroplets comprising the nanoemulsion. When administered to the patient the targeting agent will facilitate the selective localization of the nanoemulsion within the disease site where the drug is released for optimum effect. The art is silent on disease targeting thermally stabilized nanoemulsions.

Further, this invention also discloses a novel method of directly attaching various binding agents to solid lipid nanospheres. The art is silent on this method of attaching binding agents directly onto solid lipid nanospheres.

SUMMARY OF THE INVENTION

This invention describes of a novel means of stabilizing drugs by incorporating them into a "thermally stabilized nanoemulsion" that has a phase transition temperature that is at or below the body temperature of 37 C and above a storage temperature of 4-8 C. One or more lipid soluble drugs are incorporated into the oil/lipid component of the nanoemulsion at an elevated temperature above the phase transition temperature of the nanoemulsion and then stabilized for extended storage by lowering the temperature to below its phase transition temperature. This causes the nanoemulsion to transform into solid lipid nanospheres entrapping the drug within the solid lipid matrix. Upon rewarming the lipid nanospheres they will reconvert to an oil-in-water nanoemulsion suitable for administration to the patient in need. This invention further discloses disease targeting thermally stabilized nanoemulsions utilizing targeting agents such as antibodies, aptamers, binding peptides, hormones, cytokines and the like, attached to the exterior of the nanodroplets comprising the nanoemulsion.

DESCRIPTION OF THE INVENTION

The novelty of this invention is its teaching of "thermally stabilized nanoemulsion" as a means of stabilizing drugs for long-term storage. The nanoemulsion is in the form of an oil-in-water emulsion at body temperature but which becomes a finely dispersed suspension of solid lipid nanospheres when the temperature is lowered to below its phase transition temperature. This traps the drug within a solid lipid matrix and prevents its leakage during storage. Upon rewarming the lipid nanospheres to above their phase transition temperature they will reconvert into an oil-in-water nanoemulsion suitable for administration to a patient in need.

The thermally stabilized nanoemulsion has several advantages compared to other drug delivery vehicles. First, lipophilic drugs can often be incorporated into the oil/lipid component of the nanoemulsion at a higher loading dose than using liposomes which are currently the most commonly used drug delivery vehicle. Second, by trapping the drug within a solid lipid matrix the rate of diffusion of the drug is severely limited and it is thus prevented from leaking out during storage. Third, by preparing the nanodroplets of the nanoemulsion to be a particular uniform size the bioavailability and biodistribution of the incorporated drug is superior to that of the predicate free drug.

In this invention the terms "incorporated", "entrapped" and "trapping" are used to describe the various ways that the drug could be incorporated and/or associated with the nanoemulsion. For example, the drug could be entrapped within the oil/lipid component, and/or the phospholipid component, and/or associated with the surfactant and co-surfactant.

The components of the nanoemulsion typically include: one or more lipophilic drugs, one or more oils, one or more phospholipids, one or more phospholipids conjugated with polyethylene glycol polymer, and optionally one or more surfactants. The following example is provided to illustrate the general principles of how a typical thermally stabilized nanoemulsion is prepared: In one embodiment of this invention the oil used to prepare the nanoemulsion is coconut oil. Natural coconut oil has a phase transition temperature of about 26 C. A lipid soluble drug such as dactinomycin is incorporated into the coconut oil by co-dissolving the drug and the oil in an organic solvent such as a chloroform: methanol solution. In order to stabilize the nanoemulsion one or more emulsifying agents such as phosphatidylcholine (PC) and polyethylene glycol-derivatized distearoylphosphatidylethanolamine (DSPE-PEGn) where n is a molecular weight of 2,000 daltons or above) are also added and co-dissolved with the oil. The solvent is then removed by heating under vacuum leaving an oily residue. Heated distilled water is then added to the oily residue and vigorously shaken to form a coarse emulsion. The emulsion is then sonicated and extruded thru orifices of decreasing pore sizes using a commercial extruder to prepare a nanoemulsion comprised of nanodroplets having a uniform size. The uniform size of the nanodroplets can be pre-set to be a value that is within the 50 nm to 400 nm diameter range; preferably it will be in the 50 nm to 200 nm range; and most preferably it will be about 100 nm in diameter. Throughout the process the temperature is maintained above the phase transition temperature of the nanoemulsion. Typically, the process temperature is set at 70 C.

The nanodroplets prepared in this way will have the following structure. There is a central oil core containing the drug. This is surrounded by a layer of phosphatidylcholine with the tails of the phosphatidylcholine molecule embedded in the oil and the polar heads of the molecule oriented to the exterior. Also making up part of the lipid layer is the DSPE-PEGn where the DSPE component of the molecule is embedded in the oil with the PEG polymer chains extending out into the surrounding aqueous medium.

The nanoemulsion prepared using coconut oil will have a phase temperature of about 26 C. Upon cooling the nanoemulsion to below its phase transition temperature the oil will transform into a solid lipid matrix trapping the drug within the lipid matrix. The solid lipid nanospheres can now be stored for a prolonged period of time in the refrigerator set at a temperature of 4-8 C. For even longer storage the lipid nanospheres can be suspended in a suitable cryopreservative solution such as sucrose, mannose or trehalose and lyophilized. The lyophilized nanospheres can be stored frozen or refrigerated or at room temperature. They can be reconstituted by adding the appropriate amount of distilled water or a physiological solution prior to administration to the patient.

In one embodiment of this invention it may be desirable to have the phase transition temperature of the nanoemulsion set at a lower temperature than that of natural coconut oil (i.e. 26 C). To lower the phase transition temperature of the nanoemulsion a mixture of oils can be used. By mixing the correct proportions of a high temperature oil such as coconut oil with a low temperature oil such as soybean oil the final phase transition temperature of the nanoemulsion can be adjusted to any desired value between 4 C and 26 C. Other oils in varying proportions can be substituted for coconut oil and soybean oil to achieve the same effect.

In one embodiment of this invention it may be desirable to have the phase transition temperature to be above 26 C and below 37 C. One way to accomplish this is to use an oil with a high phase transition temperature such as hydrogenated coconut oil that has a phase transition temperature of about 36-40 C. The hydrogenated coconut oil can be mixed in varying proportions with oils that have low transition temperatures to yield a final transition temperature within the 26 C to 37 C range. It will be obvious to those of skill in the art that other oils or lipids with high phase transition temperatures can be mixed in varying proportions with other oils to yield a nanoemulsion whose phase transition temperature can be set at some value between 26 C and 37 C.

In one embodiment of this invention it may be desirable to have the phase transition temperature to be above 37 C. One way of doing this is to use an oil such as nutmeg oil that has a high phase transition temperature. For example, trimyristin which makes up most of nutmeg oil has a phase transition temperature of about 55 C. Nutmeg oil can be mixed in varying proportions with another oil such as coconut oil to prepare a nanoemulsion that has a final transition temperature set within the 37 C to 55 C range. It will be obvious to those of skill in the art that other oils or lipids with high phase transition temperatures can be used in lieu of nutmeg oil or hydrogenated coconut oil to prepare a nanoemulsion whose phase transition temperature can be set above 37 C.

The above examples are provided for illustration only and to teach the principles of the methodology used. It will be obvious to those of skill in the art that other oils with high phase transition temperatures can be mixed with oils with low phase transition temperatures to prepare nanoemulsions with different phase transition temperatures. For example, hydrogenated oils, long chain triglycerides, fats and waxes with high phase transition temperatures can be mixed with varying proportions of low phase transition temperature oils to yield a final phase transition temperature of a nanoemulsion that can be set to any value that is desired without departing from the spirit and scope of this invention.

The oil component of the nanoemulsion is selected from a list of plant, animal, and synthetic oils including, but not limited to: castor oil, corn oil, canola oil, soybean oil, peanut oil, olive oil, sunflower oil, coconut oil, palm oil, nutmeg oil, primrose oil, fish oil, mineral oil and triglycerides. Generally a mixture of two or more oils are used in different proportions in order to obtain the desired phase transition temperature at which the nanoemulsion will change from an oil to a solid lipid and vice versa. Optionally, in one embodiment of this invention cholesterol is included in the nanoemulsion formulation. Cholesterol has the capacity to stabilize the phospholipid layer of the nanoemulsion.

In order to obtain a stable nanoemulsion one or more emulsifying agents and surfactants are included in the formulation. The emulsifying agent is selected from a list that includes: egg phosphatidylcholine (EPC), soy phosphatidylcholine (SPC), hydrogenated soy phosphatidylcholine (HSPC), phosphatidylethanolamine (PE), phosphatidylglycerol (PG), phosphatidylinsitol (PI), monosialoganglioside and sphingomyelin (SPM); the derivatized vesicle forming lipids such as polyethylene glycol) derivatized distearoylphosphatidylethanolamine (DSPE-PEGn), polyethyleneglycol derivatized ceramides (CER-PEG), distearoylphosphatidylcholine (DSPC), and dimyristoylphosphatidylcholine (DMPC). It should be noted that different phospholipids have different phase transition temperatures and therefore the particular phospholipid selected and the amount used in the formulation will affect the final transition temperature of the nanoemulsion.

In this invention where surfactants are used the non-ionic surfactants are preferred and include: polysorbate 80 (Tween 80), polysorbate 20 (Tween 20), Poloxamer 188, Brij 35 and the like. These may be used singly or in combination. Optionally other co-surfactants such as short-chain alcohols e.g. ethanol may be added to the formulation in order to reduce the size of the nanodroplets in the nanoemulsion.

There are a large number of lipophilic drugs used to treat different diseases that can be incorporated into a thermally stabilized nanoemulsion. In this invention the term "lipophilic" or "lipid soluble" is used to describe drugs that are more soluble in oil than in water. This is typically expressed as the "partition coefficient" or "log P" of the drug. In general the higher the log P the better drug incorporation and retention of the drug within the nanoemulsion. In this invention drugs with a log P higher than 1.0 can be used; those that are higher than 2.0 are preferred; and most especially preferred are those that are higher than 3.0.

Typically these drugs are dissolved in a minimum quantity of an organic solvent such a chloroform:methanol solution and added to the oils and phospholipids mixture used to prepare the nanoemulsion. In order to obtain higher loading doses of the drug a mixture of oils containing a mixture of long, medium and short chain triglycerides and fatty acids may be used. This creates imperfections in the manner in which the molecules of different chain lengths can align with each other and thus provide "spaces" between the molecules where the drug can reside.

The relative proportions of each of the components of the formulation will affect the size and physicochemical properties of the nanoemulsion including its eventual phase transition temperature, the quantity of drug that can be incorporated, and the bioavailability and biodistribution of the drug.

There are a large variety of methods described for preparing nanoemulsions, and the means whereby a large variety of different drugs can be incorporated into said nanoemulsions. For example, drug loaded nanoemulsions can be prepared using sonication or homogenization or shearing or self-emulsifying methods. Or they can be prepared using a combination of methods such as sonication and/or homogenization to prepare an emulsion followed by an extrusion step to calibrate the final size of the nanodroplets comprising the nanoemulsion. These and other methods of nanoemulsion preparation are known to those of skill in the art and are considered to be within the scope of this invention.

The following example will illustrate the principles and means of preparing a thermally stabilized nanoemulsion incorporating a lipid soluble drug. In one embodiment of this invention a lipid soluble cancer drug is incorporated into the nanoemulsion. To prepare the nanoemulsion 10 mg of dactinomycin (which is a lipid soluble drug) is mixed with 1,000 mg coconut oil, 400 mg HSPC, 100 mg DSPE-PEG2000, and the mixture is dissolved in a small quantity of cholorform:methanol solvent. The solvent is removed under vacuum and heat using a rotary evaporator (Hei-VAP Heidolph USA) leaving an oily film. Distilled water heated to 70 degree C. is added to the oily film and vigorously shaken to form a coarse emulsion. The emulsion is sonicated in a heated waterbath sonicator and then extruded using a commercial extruder (EmulsiFlex-05, Avestin, Canada) through membranes of decreasing pore sizes until a uniform sized nanoemulsion of about 100 nm is produced. A temperature of 70 C is maintained throughout the whole process. The nanoemulsion is then allowed to cool to room temperature or below. During the cooling period the temperature of the nanoemulsion will fall below its phase transition temperature whereupon it will transform from an oil-in-water emulsion into a suspension of finely dispersed solid lipid nanospheres. Typically the suspension of lipid nanospheres is stored at 4 C; or it is lyophilized with cryoprotectants such as sucrose or mannose or trehalose and stored at 4 C or colder for long term storage.

In this invention the uniform calibrated size of the nanodroplets will lie in the 50 nm-300 nm range, preferably in the 50 nm-200 nm range and most preferably about 100 nm in diameter. The size of the nanodroplets is critical when developing targeting biopharmaceuticals that will be administered parenterally. If the nanodroplets are too large i.e. over 300 nm they are rapidly taken up by the liver and reticuloendothelial system and removed from the circulation. Smaller nanodroplets about 100 nm in size will remain in the blood circulation for a longer period of time. Also in this invention the surface of the nanodroplets are coated with a phospholipid bearing hydrophilic PEG chains that provide steric hindrance to recognition by the liver and the immune system. This will serve to protect the nanodroplets from degradation by the liver and removal by the immune system, thus allowing more of the drug to be bioavailable for a longer period of time.

The smaller sized nanodroplets (100 nm) will circulate in the blood stream because they are too large to extravasate thru the endothelial pores of normal blood capillaries supplying normal healthy tissues. However, tumors are often served by blood vessels that have very enlarged endothelial pores (e.g. 400 nm or more). When the nanodroplets reach these "leaky" blood capillaries they can extravasate out of the blood vessels and into the tumor where the incorporated drug is released for optimum effect. At the same time less drug can penetrate into normal tissues and cause harm.

It will be obvious to those of skill in the art from the teaching of this invention that other lipophilic cancer drugs can be incorporated in like manner into a thermally stabilized nanoemulsion. These variations are therefore considered to be within the spirit and scope of this invention.

It will be obvious to those of skill in the art that there are numerous lipophilic drugs available that can be similarly incorporated into the stabilized nanoemulsion of this invention and used to treat a variety of different diseases. For example, these include anti-cancer drugs; anti-diabetes drugs; anti-bacterial drugs; anti-viral drugs; anti-inflammatory drugs; anti-hypertensive drugs; cholinergic drugs; adrenergic drugs; anti-hyperlipidemic drugs; anti-depressive drugs; anti-psychotic drugs; anaesthetic drugs; and analgesics drugs.

In one embodiment of this invention two or more lipophilic cancer drugs are incorporated into the nanoemulsion. For example, it is well-known in cancer chemotherapy that different cancer drugs used in combination appear to have a superior effect compared to treatment with a single cancer drug. Therefore it seems likely that two or more cancer drugs incorporated into a stabilized nanoemulsion would also have a beneficial therapeutic outcome. For example, the lipophilic cancer drugs dactinomycin and docetaxel can be mixed together and incorporated into a stabilized nanoemulsion using essentially the same formulation and process described earlier. It will be obvious to those of skill in the art from the teaching of this invention that other lipophilic cancer drugs can be mixed together and incorporated in like manner into a thermally stabilized nanoemulsion. These variations are therefore considered to be within the spirit and scope of this invention.

In one embodiment of this invention the two or more lipophilic cancer drugs incorporated into the nanoemulsion are selected to target different phases in the cell-cycle of the tumor cell. This will increase the number of tumor cells that can be killed at one time. Further the incorporation of the drugs into a lipid matrix will result in a more extended period of drug release. Those tumor cells that survived the initial drug exposure because they were in a phase that was not targeted would subsequently enter a targeted phase and be killed by the residual drugs present within the tumor. The administration of multiple different cancer drugs simultaneously into the patient will result in increased efficacy while at the same time their incorporation into a nanoemulsion will result in reduced cytotoxicity to the patient.

In one embodiment of this invention certain lipophilic compounds that can potentiate drug cytotoxicity can also be incorporated into the thermally stabilized nanoemulsion. For example, acid ceramidase inhibitors (ACD) when administered in combination with a cancer drug increases the cytotoxicity of the drug upon tumor cells.

It will also be obvious to those of skill in the art that for any disease treated with multiple drugs that providing that these drugs were lipophilic then they could be combined together in a thermally stabilized nanoemulsion and used to treat that disease. These variations are therefore considered to be within the spirit and scope of this invention In one embodiment of this invention the development of a disease targeting thermally stabilized nanoemulsion is disclosed. A targeting agent such as a disease targeting antibody is attached to the exterior of the nanodroplets comprising the nanoemulsion. When administered to the patient the disease targeting nanoemulsion will extravasate thru the leaky capillaries of the diseased site where the targeting antibody will bind to its target and anchor the nanoemulsion there. Depending on the particular targeting agent employed the drug may be internalized and/or released within the diseased site for optimum effect. This could improve the safety and efficacy characteristics of many of the known small molecule drugs in current use today.

To prepare a disease targeting thermally stabilized nanoemulsion the same materials and methods that were used to prepare a thermally stabilized nanoemulsion are employed with the following modifications: A small amount of DSPE-PEG-MAL is added to the nanoemulsion formulation and the procedure is performed as disclosed earlier. The nanoemulsion produced has the DSPE component of the DSPE-PEG-MAL molecule embedded within the surface layer of nanodroplets with the distal PEG end of the molecule bearing the exposed maleimide site. A targeting agent, such as the Fab fragment of a disease targeting antibody is then conjugated to the maleimide thus anchoring the antibody to the surface of the nanospheres. The Fab fragment becomes attached in such a manner that its antigen binding site is free to bind to its target.

An alternative method of attaching the Fab to the nanoemulsion is the "post-insertion method". In this method the thermally stabilized nanoemulsion is prepared as described earlier but with the MAL-PEG-DSPE omitted from the lipid mixture. The Fab fragment is bound to the MAL-PEG-DSPE in a separate reaction. The Fab-MAL-PEG-DSPE moiety is then allowed to react with the stabilized nanoemulsion at a temperature that is higher than the transition temperature of the nanoemulsion whereupon the DSPE end of the moiety will insert into the lipid layer of the nanoemulsion thus anchoring the Fab to the nanoemulsion thru the PEG link. The Fab fragment becomes attached in such a manner that its antigen binding site is free to bind to its target.

In one embodiment of this invention a novel method of attaching the disease targeting antibody to lipid nanospheres is disclosed. First, the drug nanoemulsion with DSPE-PEG-MAL included is prepared as described earlier. The nanoemulsion is then cooled below its transition temperature which transforms the nanodroplets into lipid nanospheres with the DSPE component of the DSPE-PEG-MAL molecule embedded within the surface layer of the lipid nanosphere with the distal PEG end of the molecule bearing the exposed maleimide site. A targeting agent, such as the Fab fragment of a disease targeting antibody is then conjugated to the maleimide thus anchoring the antibody to the surface of the nanospheres. Upon rewarming the disease targeting nanospheres to above their phase transition temperature they will convert into a disease targeting oil-in-water nanoemulsion.

To prepare the targeting antibody in a form suitable for conjugation to the maleimide site it is first purified using standard laboratory methods e.g. gel-filtration, affinity chromatography etc. The Fab fragment of the antibody is then prepared using immobilized papain to digest the antibody into its Fab and Fc fragments followed by the removal of the Fc fragment using immobilized Protein A. The purified Fab is then incubated with the prepared nanoemulsion or nanospheres (e.g. overnight at 4° C.) to allow binding of the Fab to the maleimide site on the DSPE-PEG.-MAL molecules attached to the surface of the nanodroplets or nanospheres. Any unreacted material is removed by dialysis or column chromatography. Upon cooling to below its phase transition temperature the suspension of nanospheres are stored at 4 degree C. or lyophilized for long term storage.

It will be obvious to those of skill in the art that there are other well-known methods of conjugating the antibody to the exterior surface of the thermally stabilized nanoemulsion that can be utilized without departing from the spirit and scope of this invention.

In one embodiment of this invention the tumor targeting antibody is an antibody that will target Human Epidermal Growth Factor Receptor 2 (HER2) present on breast cancer cells. HerceptinR (trastuzumab) is a commercially available humanized monoclonal antibody that targets HER2 that are over-expressed on certain breast cancers. Anti-HER2 antibody and biosimilar versions can be used to prepare tumor targeting thermally stabilized nanoemulsions using the general methods described in this invention. These nanoemulsions will have the capacity to bind to breast cancer cells and anchor the nanoemulsion within the tumor. They will also have the additional advantage that by binding to the cancer cells they may inhibit tumor growth. It is also postulated that this effect is enhanced due to the cell bound nanoemulsion being internalized by the cancer cells where it will have maximum effect. Tumor targeting nanoemulsions prepared using anti-HER2 antibody may therefore be the preferred pharmaceutical in treating breast cancer.

In one embodiment of this invention the tumor targeting antibody is an antibody that will target Human Epidermal Growth Factor Receptor 1 (EGFR1). Erbitux® (cetuximab) is a commercially available chimeric human/mouse monoclonal antibody that will target EGFR over-expressed in colorectal cancer and squamous cell carcinoma of the head and neck. VectibixR (panitumumab) is a fully human monoclonal antibody that also targets EGFR in metastatic colorectal cancer. Anti-EGFR antibody and biosimilar versions can be used to prepare tumor targeting thermally stabilized nanoemulsions using the general methods described in this invention. The nanoemulsion prepared using anti-EGFR antibody will have the capacity to bind to the cancer cells and anchor the nanoemulsion within the tumor. They will also have the additional advantage that by binding to the cancer cells they can inhibit its growth. It is also postulated that this effect is enhanced due to the cell bound nanoemulsion being internalized by the cancer cells where it will have maximum effect. Tumor targeting nanoemulsions prepared using anti-EGFR antibody may therefore be the preferred pharmaceutical in treating colorectal cancer and squamous cell carcinoma of the head and neck.

In one embodiment of this invention the tumor targeting antibody is an autoimmune antinuclear antibody (ANA) that targets the extracellular nuclear material that is present in the necrotic regions of solid tumors. The ANA is collected from patients with systemic lupus erythematosus (SLE) and purified using salt-fractionation and immunoaffinity methods. The Fab fragment of the antibody is prepared and attached to the thermally stabilized nanoemulsion thru a MAL-PEG-DSPE link as described earlier. The ANA nanoemulsion prepared in this manner will concentrate within the areas of necrosis present in solid tumors where the drugs are released over time to kill surrounding cancer cells. As almost all solid tumors will have areas of necrosis the ANA nanoemulsion may be utilized to treat a wide variety of different types of solid tumors including breast cancer, prostate cancer, lung cancer, colon cancer, lung cancer, liver cancer, melanoma and other solid tumors.

There are a growing number of new antitumor antibodies being developed that can be used to prepare tumor targeting nanoemulsions. For example, many antitumor antibodies are known to target certain cell surface markers present on tumor cells. These can be attached to the drug nanoemulsions using the general principles outlined in this invention There are a wide variety of different disease targeting antibodies that have been identified. These include, but are not limited to, the antibodies directed against bacteria, viruses and other pathogens; and also including, but not limited to, the antibodies directed against cell proteins such as anti-tumor antibodies; anti-growth factor receptor antibodies, anti-cytokine receptor antibodies and anti-cell surface marker antibodies.

The antibodies may be polyclonal, monoclonal or prepared as a recombinant protein. In this invention the term "antibody" is used to include the whole antibody molecule, and/or the binding fragment (Fab and Fab2) of the antibody molecule and/or a recombinant protein that has antigen binding capacity.

It will be also obvious to those of skill in the art that other targeting agents that mimic the binding capacity of antibodies can be employed to prepare disease targeting nanoemulsions. These binding agents include aptamers, binding peptides, soluble receptors and the like. It will also be obvious to those of skill in the art that targeting ligands such as hormones, growth factors, cytokines and the like can similarly be used to prepare disease targeting nanoemulsions. In this invention the term "disease targeting thermally stabilized nanoemulsion" is used to include all categories of targeting nanoemulsions including those coated with antibodies; or aptamers, or binding peptides, or hormones, or growth factors and the like.

Aptamers are small (i.e. 40-100 bases), synthetic single-stranded oligonucleotides (ssDNA or ssRNA) that can specifically recognize and bind to virtually any kind of target, including ions, whole cells, drugs, toxins, low-molecular-weight ligands, peptides, and proteins. Each aptamer has a unique configuration as a result of the composition of the nucleotide bases in the chain causing the molecule to fold in a particular manner. Because of their folded structure each aptamer will bind selectively to a particular ligand in a manner analogous to an antibody binding to its antigen. Aptamers are usually synthesized from combinatorial oligonucleotide libraries using in vitro selection methods such as the Systematic Evolution of Ligands by Exponential Enrichment (SELEX). This is a technique used for isolating functional synthetic nucleic acids by the in vitro screening of large, random libraries of oligonucleotides using an iterative process of adsorption, recovery, and amplification of the oligonucleotide sequences. The iterative process is carried out under increasingly stringent conditions to achieve an aptamer of high affinity for a particular target ligand. In order to improve stability against nucleases found in vivo the oligonucleotides may be modified to avoid nuclease attack. They may for example be synthesized as L-nucleotides instead of the natural D-nucleotides and thus avoid degradation from the natural nucleases. The aptamer can be synthesized with a thiol (S-S)-modified 5' end to enable it to react with the DSPE-PEG-MAL polymer and thus become attached to surface of the nanodroplets or lipid nanospheres while leaving the aptamer capable of binding to its ligand. The aptamer coated stabilized nanoemulsion is cooled to below is phase transition temeprature prior to storage in the cold. Upon rewarming the aptamer coated lipid nanospheres will convert into a disease targeting nanoemulsion.

Binding peptides consist of a chain of aminoacids that fold in such a manner that their configuration makes them capable of binding to antigens in a manner that mimics the binding of an antibody to its antigen. There are various well-known methods for preparing synthetic or biological peptide libraries composed of up to a billion different sequences, and for identifying a particular peptide sequence that will target a particular antigen. The binding peptide can be produced with a thiol group at one end to enable it to bind to the DSPE-PEG-MAL polymer and thus become attached to surface of the nanodroplets or lipid nanospheres and still retain the capacity to bind to its respective target. The binding peptide coated stabilized nanoemulsion is cooled to below its phase transition temperature prior to stoarge in the cold. Upon rewarming the binding peptide coated lipid nanospheres will convert into a disease targeting nanoemulsion.

Soluble receptors are another form of targeting agent that can be utilized to prepare a disease targeting nanoemulsion. Cells communicate by producing biological messengers such as hormones, cytokines and growth factors that bind to their specific receptors on cells causing them to respond in some fashion. There is increasing evidence that under certain conditions these receptors can become detached from the cell and circulate in the blood-stream. These "soluble" receptors can be used to target areas where there is a localized concentration of messengers being produced. For example, a tumor that is producing an excessive amount of Vascular Endothelial Growth Factor (VEGF) can be targeted using a soluble VEGF-receptor (sVEGFR) protein attached to the nanoemulsion. Similarly, an inflamed site such as an arthritic joint that is producing an excessive amount of Tumor Necrosis Factor (TNF) can be targeted using a soluble TNF-receptor (sTNFR) protein attached to the nanoemulsion. The means of attaching proteins to the nanoemulsion are well-known to those of skill in the art.

Other examples of targeting agents include hormones, cytokines and growth factors. Cells communicate by producing biological messengers such as hormones, cytokines and growth factors that bind to their specific receptors on cells causing them to respond in some fashion. These ligands can be utilized to prepare disease targeting nanoemulsions that will target cells bearing specific receptors. For example, a hormone such as estrogen attached to the nanoemulsion can be used to target breast cancer cells. Similarly a cytokine such as VEGF attached to the nanoemulsion can be used to target abnormal vascular proliferation. The means of attaching these ligands to the nanoemulsion are well-known to those of skill in the art.

Finally there are examples of certain substances such as folic acid and transferrin that appear to be selectively taken up by cancer cells compared to normal cells. These can be utilized as targeting agents for the disease targeting nanoemulsion. The means of attaching these compounds to the nanoemulsion are well-known to those of skill in the art.

The thermally stabilized nanoemulsion of this invention can be administered topically, orally, or by subcutaneous or intramuscular injection, or intravenously by injection or infusion. For disease targeting nanoemulsions the intravenous injection or infusion mode of administration is preferred. Prior to administration the lipid nanospheres in suspension are typically rewarmed to form a nanoemulsion before it is injected intravenously into the patient; or the lipid nanospheres are added to an infusion solution that is at room temperature whereupon it forms a nanoemulsion before it is infused intravenously into the patient. In certain circumstances where the nanoemulsion is prepared to have a phase transition temperature that is higher than room temperature the nanosphere suspension is either injected intravenously, or added to the infusion solution and administered intravenously as a diluted nanosphere suspension. The dosage required and the mode of administration used will depend upon the clinical condition of the patient in need.

This invention teaches a drug delivery system utilizing a particular kind of thermally stabilized nanoemulsion that can incorporate a wide variety of lipophilic drugs. It also teaches that this system can also be modified into a disease targeting delivery system that can be used to treat a variety of different diseases. It will be obvious to those of skill in the art that there are various modifications and applications that can be made from the teachings herein without departing from the spirit and scope of this invention. Accordingly, said changes and modifications are considered to lie within the scope of this invention.

What is claimed is:

1. A thermally stabilized antinuclear antibody-linked dactinomycin nanoemulsion wherein said nanoemulsion is formulated to have a phase transition temperature that is below 37 C and above 8 C; and wherein the nanodroplets comprising said nanoemulsion are uniformly sized to be 50 to 300 nm in diameter and are composed of a) dactinomycin, b) one or more oils, c) one or more phospholipids, d) DSPE-PEG2,000, e) DSPE-PEG2,000-Maleimide, and f) are coated with the Fab fragment of the antinuclear antibody.

2. A thermally stabilized antinuclear antibody-linked dactinomycin nanoemulsion according to claim 1 wherein the one or more oils are selected from the group consisting of: castor oil, corn oil, canola oil, soybean oil, peanut oil, olive oil, sunflower oil, coconut oil, palm oil, nutmeg oil, primrose oil, fish oil, mineral oil and triglycerides.

3. A thermally stabilized antinuclear antibody-linked dactinomycin nanoemulsion according to claim 1 wherein the one or more phospholipids are selected from the group consisting of: egg phosphatidylcholine (EPC), soy phosphatidylcholine (SPC), hydrogenated soy phosphatidylcholine (HSPC), phosphatidylethanolamine (PE), phosphatidylglycerol (PG), phosphatidylinositol (PI), monosialoganglioside and sphingomyelin (SPM); the derivatized vesicle forming lipids such as polyethylene glycol) derivatized distearoylphosphatidylethanolamine (DSPE-PEGn), polyethyleneglycol derivatized ceramides (CER-PEG), distearoylphosphatidylcholine (DSPC), and dimyristoylphosphatidylcholine (DMPC).

4. A thermally stabilized antinuclear antibody-linked dactinomycin nanoemulsion according to claim 2 wherein the oil is natural coconut oil that has a phase transition temperature of 26 C, or hydrogenated coconut oil that has a phase transition temperature of 36 C.

5. A thermally stabilized antinuclear antibody-linked dactinomycin nanoemulsion according to claim 3 wherein the phospholipid is hydrogenated soy phosphatidylcholine (HSPC).

6. A thermally stabilized antinuclear antibody-linked dactinomycin nanoemulsion according to claim 1, wherein a therapeutic dosage of said nanoemulsion is administered by intravenous injection or infusion to a cancer patient in need.

* * * * *